United States Patent [19]

Westlake

[11] Patent Number: 4,513,740
[45] Date of Patent: Apr. 30, 1985

[54] THERAPEUTIC STOCKING AND METHOD OF PLACEMENT

[75] Inventor: Betsy C. Westlake, Palatine, Ill.
[73] Assignee: The Kendall Company, Boston, Mass.
[21] Appl. No.: 654,489
[22] Filed: Sep. 26, 1984

Related U.S. Application Data

[63] Continuation of Ser. No. 391,195, Jun. 23, 1982, abandoned.

[51] Int. Cl.³ ............................................. A61F 13/08
[52] U.S. Cl. ................................................. 128/165
[58] Field of Search ............... 128/82, 156, 157, 165, 128/166; 2/239, 240, 224; 66/172 E, 178 A, 178 R

[56] References Cited

U.S. PATENT DOCUMENTS

| | | | |
|---|---|---|---|
| 1,488,379 | 3/1975 | Chaffee | 128/165 |
| 3,605,122 | 9/1971 | Myers | 2/239 |
| 3,856,008 | 12/1974 | Fowler et al. | 361/42 |

FOREIGN PATENT DOCUMENTS 547045  3/1932  Fed. Rep. of Germany ...... 128/165

Primary Examiner—John D. Yasko
Assistant Examiner—Christa K. Scott
Attorney, Agent, or Firm—Powell L. Sprunger

[57] ABSTRACT

A therapeutic stocking comprising, a first circumferential segment for placement on the leg below the knee, with the first segment extending from the ankle to a point slightly below the knee. The first segment exerts a compressive pressure on the wearer's leg gradually decreasing from the ankle to said point below the knee. The stocking has a second circumferential segment for placement on the leg above the knee, with the second segment extending from a point slightly above the knee to the upper thigh. The method of placement of a therapeutic stocking on a wearer's leg includes the steps of measuring the circumference of the wearer's leg at two locations, placing an elastic fabric panel having overlapping side edges about the wearer's leg, the upper and lower ends of the panel having indicia representing a number of possible selected circumferential measurements of a wearer's leg, and securing the side edges of the panel together with the side edges overlapped to match the two previously determined circumferential measurements of the wearer's leg. The second segment exerts a compressive pressure on the wearer's leg gradually decreasing from said point above the knee to the upper thigh.

8 Claims, 3 Drawing Figures

THERAPEUTIC STOCKING AND METHOD OF PLACEMENT

This is a continuation of application Ser. No. 391,195, filed June 23, 1982 now abandoned.

BACKGROUND OF THE INVENTION

The present invention relates to elastic garments, and more particularly to therapeutic stockings.

In the recent past, therapeutic stockings have been prescribed on a relatively wide scale to prevent possible embolism in a patient. When a patient is confined to bed, for example, after an operation, the likelihood of thrombis is markedly increased due to a decrease in the velocity of blood flow in the patient's legs during confinement. Therapeutic or anti-embolism stockings cause application of a compressive pressure against the patient's leg which gradually decreases from the ankle toward the upper part of the leg. Such stockings increase the velocity of blood flow in the legs, and minimize the possibility of thromboembolism.

It has been found that the prior stockings have been frequently difficult to place on the patient's leg by the hospital personnel. Also, it is desirable to avoid restrictive pressures on the veins in the sensitive popliteal space in the knee region. A stocking which exerts a reduced pressure in the knee region is disclosed in U.S. Pat. No. 3,889,494, incorporated herein by reference.

SUMMARY OF THE INVENTION

A principal feature of the present invention is the provision of an improved therapeutic stocking of simplified construction.

The stocking of the present invention comprises, a first circumferential segment for placement on the leg below the knee, with the first segment extending from the ankle to a point slightly below the knee and covering the calf. The first segment comprises a knitted fabric including an elastomeric yarn which exerts a compressive pressure on the wearer's leg gradually decreasing from the ankle to said point below the knee. The stocking has a second circumferential segment for placement on the leg above the knee, with the second segment extending from a point slightly above the knee to the upper thigh and covering the lower thigh. The second segment comprises a knitted fabric including an elastomeric yarn which exerts a compressive pressure on the wearer's leg gradually decreasing from said point above the knee to the upper thigh.

A feature of the present invention is that the stocking is more easy to apply to a patient's leg than prior stockings.

Another feature of the invention is that the stocking does not exert pressure on the veins in the sensitive popliteal space.

Still another feature of the invention is that the first and second segments may comprise panels which are releasably secured about the wearer's leg.

Yet another feature of the invention is that the panels may be adjusted to the wearer's leg depending upon the circumference of the leg.

Further features will become more fully apparent in the following description of the embodiments of this invention and from the appended claims.

DESCRIPTION OF THE PREFERRED EMBODIMENTS

Figure 1:
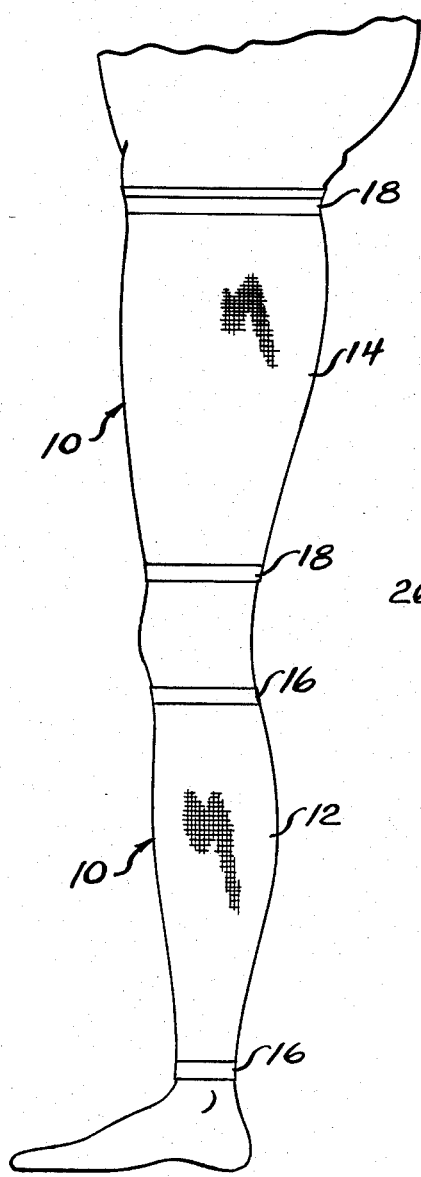
FIG. 1 is a perspective view of one embodiment of the stocking of the present invention.

Referring now to FIG. 1, there is shown a therapeutic stocking generally designated 10 having a lower first circumferential generally cylindrical segment 12, and an upper second circumferential generally cylindrical segment 14. As shown, the first segment 12 is placed on the leg below the knee, and the second segment 14 is placed on the leg above the knee.

The first segment 12 extends from the ankle to a point slightly below the knee and covers the calf. The first segment 12 comprises a knitted fabric including an elastomeric yarn which exerts a compressive pressure on the wearer's leg gradually decreasing from the ankle to said point below the knee. The first segment 12 may have a pair of non-compressive welts 16 at the lower and upper ends of the first segment 12.

The second segment 14 extends from a point slightly above the knee to the upper thigh and covers the lower thigh. The second segment 14 comprises a knitted fabric including an elastomeric yarn which exerts a compressive pressure on the wearer's leg gradually decreasing from said point above the knee to the upper thigh, with the pressure at the point above the knee being less than the pressure at the point below the knee. The second segment 14 may have a pair of non-compressive welts 18 at the lower and upper ends of the second segment 14.

Thus, in accordance with the present invention, the stocking 10 exerts a compressive pressure which gradually decreases from the ankle to a point below the knee and from a point above the knee to the lower thigh. The stocking 10 of the present invention is more simple to place on a wearer's leg than prior stockings. Also, the stocking 10 of the present invention does not exert restrictive pressures on the veins in the sensitive popliteal space in the knee region.

Figure 2:
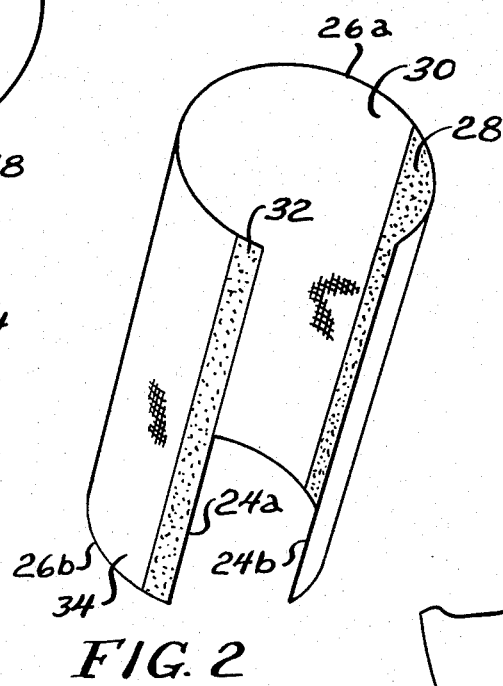
FIG. 2 is a perspective view of another embodiment of the stocking of the present invention.
Figure 3:
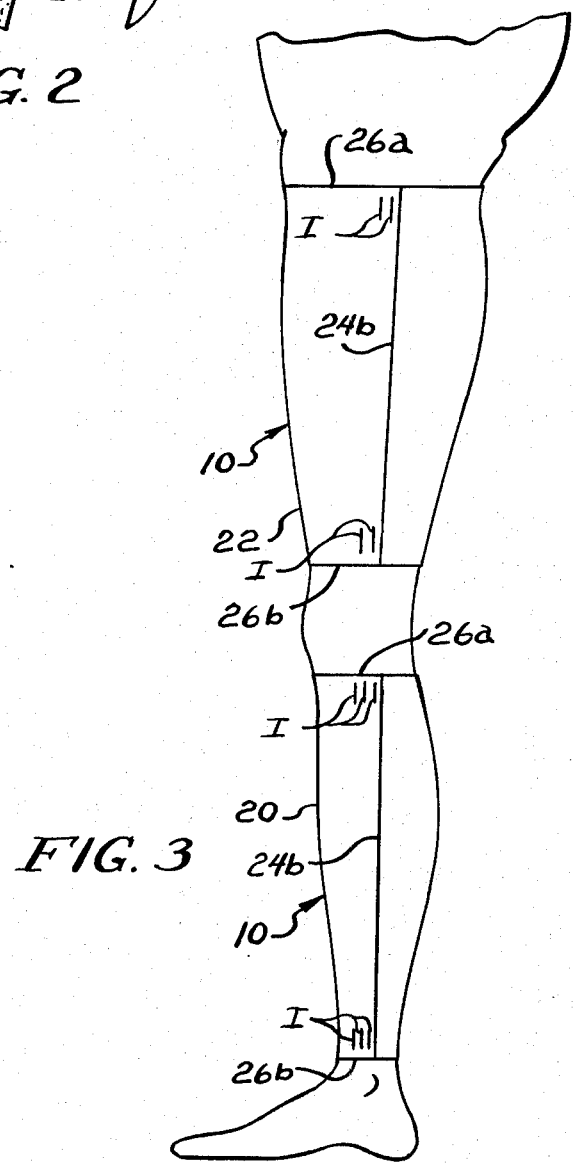
FIG. 3 is a perspective view illustrating the stocking of FIG. 2 as applied to a wearer's leg.

Another embodiment of the present invention is illustrated in FIGS. 2 and 3, in which like reference numerals designate like parts. In this embodiment, the stocking 10 comprises a first lower panel 20 of elastic fabric for placement below the knee, and a second upper panel 22 of elastic fabric for placement above the knee.

The first and second panels 20 and 22 have a pair of opposed side edges 24a and 24b, and a pair of opposed end edges 26a and 26b connecting the side edges 24a and b. The panels 20 and 22 have a first loop fastening strip 28 extending along the side edge 24b on an inner surface 30 of the panels 20 and 22. Also, the panels 20 and 22 have a second hook fastening strip 32 extending along the side edge 24a on an outer surface 34 of the panels 20 and 22. The first and second fastening strips 28 and 32 may be of the type sold under the trademark Velcro. In an alternative form, the strip 28 may comprise a hook fastening strip and the strip 32 may be omitted, with the hook strip 28 being secured directly to the fabric of the stocking.

The lower first panel 20 has a sufficient width between the side edges 24a and b to encircle the leg below the knee in an overlapping relationship. The first panel 20 has a sufficient length between the end edges 26a and b to extend from the ankle to a point slightly below the knee. The second panel 22 has a sufficient width between the side edges 24a and b to encircle the leg above the knee in an overlapping relationship. The second panel 22 has a sufficient length between the end edges 26a and b to extend from a point slightly above the knee to the upper thigh.

With reference to FIG. 3, the first panel 20 is secured about the wearer's leg below the knee by use of the fastening strips 28 and 32, and the second panel 22 is secured about the wearer's leg above the knee through use of the fastening strips 28 and 32. As shown, the panels 20 and 22 may have indicia I at the lower and upper ends thereof to facilitate placement of the panels 20 and 22 about the wearer's leg. The indicia I may include vertical lines, as shown, along with numerals associated with the lines indicating the circumference of the wearer's leg in the region of the indicia I. Thus, the circumference of the wearer's leg may be measured by a suitable tape, and the panels 20 and 22 may be secured about the leg with the side edge 24b located at the appropriate indicia I associated with the numeral indicating the leg's circumference in the region of the indicia I.

When properly placed on the wearer's leg, the lower panel 20 exerts a compressive pressure which gradually decreases from the patient's ankle to the point below the knee, and the upper panel 22 exerts a compressive pressure against the wearer's leg which gradually decreases from the point above the knee to the upper thigh. As before, the stocking 10 of FIGS. 2 and 3 is more easy to place on the wearer's leg than prior stockings. Further, the stocking 10 of FIGS. 2 and 3 does not exert a restrictive pressure against the veins in the sensitive popliteal space in the knee region.

The foregoing detailed description is given for clearness of understanding only, and no unnecessary limitations should be understood therefrom, as modifications will be obvious to those skilled in the art.

I claim:

1. A therapeutic stocking, comprising:
   a first circumferential panel segment for placement on the leg below the knee, said first panel having a pair of substantially straight opposed side edges and a pair of opposed end edges connecting the side edges, said first panel having a sufficient width between said side edges to encircle the leg below the knee in overlapping relationship, said first panel having a sufficient length between said end edges to extend from the ankle to a point slightly below the knee, said first panel segment comprising a knitted fabric including an elastomeric yarn which exerts a compressive pressure on the wearer's leg gradually decreasing from the ankle to said point below the knee, and means for releasably securing the first panel about the leg below the knee such that said first panel is assured to exert said compressive pressure on the wearer's leg, gradually decreasing from the ankle to said point below the knee, said means for releasably securing said first panel about the leg including indicia means adjacent the lower and upper ends thereof for representing a selected number of possible circumferential measurements of a wearer's leg at the ankle and an area just below the knee, whereby, after a determination of the circumference of a selected wearer's ankle and at an area just below the knee, said first panel may be placed about the lower leg with the side edges overlapped to match the circumference of the wearer's leg in the region of said indicia, thus to assure said compressive pressure is properly applied to the wearer's lower leg; and
   a second circumferential panel segment for placement on the leg above the knee, said second panel having a pair of substantially straight opposed side edges and a pair of opposed end edges connecting the side edges, said second panel having a sufficient width between said side edges to encircle the leg above the knee in overlapping relationship, said second panel having a sufficient length between said end edges to extend from a point slightly above the knee to the upper thigh, said second panel segment comprising a knitted fabric including an elastomeric yarn which exerts a compressive pressure on the wearer's leg gradually decreasing from said point above the knee to the upper thigh, and means for releasably securing the second panel about the leg above the knee such that said second panel is assured to exert said compressive pressure on the wearer's leg, gradually decreasing from said point above the knee to the upper thigh, said means for releasably securing said second panel about the leg including indicia means adjacent the lower and upper ends thereof for representing a selected number of possible circumferential measurements of a wearer's leg at an area just above the knee and about the upper thigh, whereby said second panel may be placed about the upper leg with the side edges overlapped to match the circumference of the wearer's leg in the region of the indicia, thus to assure said compressive pressure is properly applied to the wearer's upper leg.

2. The stocking of claim 1 wherein said first and second segments include a welt at the lower and upper ends of the segments.

3. The stocking of claim 1 wherein the pressure at the point above the knee is less than the pressure at the point below the knee.

4. The stocking of claim 1 wherein the securing means of the first and second segments comprises a hook strip extending along one of said side edges, and a loop strip extending along the other of said side edges.

5. A method of applying a predetermined amount of compressive pressure to the leg of a wearer comprising the steps of:
   measuring the circumference of a wearer's leg at two, predetermined locations of the leg, spaced a predetermined distance apart, which spacing represents a specific length portion of the wearer's leg against which a compressive force is to be applied;
   encircling the specific length portion of the wearer's leg with a therapeutic stocking comprising a panel of elastic fabric having a pair of substantially straight opposed side edges and a pair of opposed lower and upper end edges connecting the side edges, the panel having a length between the end edges equivalent to the length portion of the wearer's leg against which the compressive force is to be applied, the panel having a sufficient width to encircle the length portion of the wearer's leg in overlapping relationship, the elastic fabric of the panel being such that, when the panel is wrapped about the wearer's leg portion and the side edges are secured together, a compressive pressure is exerted on the wearer's leg portion, gradually decreasing from the panel lower end edge to the panel upper end edge, there being means for releasably securing the panel about the wearer's leg portion including indicia adjacent the upper and lower ends of the panel which represent a selected number of possible circumferential measurements of a wearer's leg at the predetermined locations on the leg; and securing the panel about the specific length portion of the wearer's leg with the side edges overlapped to match the circumference of the wearer's leg in the region of the indicia, thus to assure the compressive pressure is properly applied the the wearer's leg.

6. The method of applying compressive pressure as recited in claim 5 wherein the predetermined locations are the ankle and a point just below the knee of the wearer, and the panel is secured about the lower leg of the wearer, between the ankle and a point just below the knee.

7. The method of applying compressive pressure as recited in claim 6 wherein the predetermined locations are a point slightly above the knee and the upper thigh of the wearer, and the panel is secured about the upper leg of the wearer, between a point just above the knee and the upper thigh.

8. The method of applying compressive pressure as recited in claim 6 wherein compressive pressure is applied to two specific length portions of a wearer's leg, there being two of the panels secured about the wearer's leg, a first panel being secured about the lower leg, between the ankle and a point just below the knee and a second panel being secured about the upper leg, between a point just above the knee and the upper thigh, the circumference of the leg being measured at the ankle and a point just below the knee for proper placement and securement of the first panel, the circumference of the leg also being measured at a point slightly above the upper knee and the upper thigh for proper placement and securement of the second panel.

* * * * *